United States Patent [19]

Nipe et al.

[11] 4,225,739

[45] Sep. 30, 1980

[54] PROCESS FOR IMPROVING OLEFIN POLYMER OIL PROPERTIES

[75] Inventors: Richard N. Nipe; John W. Schick, both of Cherry Hill; Robert M. Gemmill, Jr., Pitman, all of N.J.

[73] Assignee: Mobil Oil Corporation, New York, N.Y.

[21] Appl. No.: 21,412

[22] Filed: Mar. 19, 1979

Related U.S. Application Data

[63] Continuation-in-part of Ser. No. 848,968, Nov. 7, 1977, abandoned.

[51] Int. Cl.² ............................................... C07C 3/18
[52] U.S. Cl. ..................................... 585/525; 585/903
[58] Field of Search ................................ 585/525, 903

[56] References Cited

U.S. PATENT DOCUMENTS

| | | | |
|---|---|---|---|
| 3,119,884 | 1/1964 | Allen et al. | 585/517 |
| 3,991,129 | 11/1976 | Daniels | 585/504 |
| 3,997,621 | 12/1976 | Brennan | 585/255 |

*Primary Examiner*—C. Davis
*Attorney, Agent, or Firm*—Charles A. Huggett; James F. Powers, Jr.; Hastings S. Trigg

[57] ABSTRACT

Polymer oils having reduced viscosity and increased viscosity index are produced by oligomerizing a mixture of short chain 1-olefins and long chain 1-olefins in the presence of water or alcohol promoted boron trifluoride catalyst and low-boiling recycle from a previous oligomerization run.

4 Claims, No Drawings

PROCESS FOR IMPROVING OLEFIN POLYMER OIL PROPERTIES

CROSS REFERENCE TO RELATED APPLICATIONS

This application is a continuation-in-part of copending application Ser. No. 848,968, filed Nov. 7, 1977, and now abandoned.

BACKGROUND OF THE INVENTION

1. Field of the Invention

This invention is concerned with the oligomerization of certain olefin mixtures to produce synthetic lubricant base stocks having improved viscosity characteristics.

2. Description of the Prior Art

In polymerization and oligomerization processes, recycle of light boiling fractions to the process has been used for increasing ultimate yield, hopefully without degrading the physical properties of the finished product. In the oligomerization of mixtures of short chain and long chain 1-olefins in the presence of Friedel-Crafts catalysts to produce super-quality synthetic lubricants, it was found that with catalysts, such as aluminum chloride, the use of recycle did indeed increase ultimate yield. The physical properties of the finished product, however, were either unfavorable or showed little change compared with properties obtained when recycle operation was not used. On the other hand, when water or alcohol promoted boron trifluoride catalyst was used, product yield remained essentially the same. Unexpectedly, however, fluid viscosity markedly decreased, accompanied by improvement in viscosity index. Both properties are considered highly important for a high quality synthetic lubricant.

SUMMARY OF THE INVENTION

This invention provides a process for producing lubricants having low viscosity and high viscosity index that comprises oligomerizing a mixture of short chain 1-olefins, long chain 1-olefins, and low-boiling recycle from a previous oligomerization run in the presence of boron trifluoride catalyst promoted with water or alcohol.

DESCRIPTION OF SPECIFIC EMBODIMENTS

As indicated hereinbefore, the charge to the process of this invention is a mixture of one or more short chain 1-olefins, one or more long chain 1-olefins, and recycle. The utilizable short chain 1-olefin is an olefin like propylene, which can contain one or more 1-olefins such as 1-butene, 1-pentene, and 2-methyl-1-butene. Propylene is particularly preferred.

The long chain 1-olefins have between 14 and 20 carbon atoms. Typical long chain 1-olefins include 1-tetradecane, 1-pentadecane, 1-hexadecane, 1-heptadecene, 1-octadecene, and 1-eicosene. The long chain 1-olefins are commercially available in mixtures of two or more such olefins and such mixtures are utilizable herein.

The recycle used herein is obtained from a previous oligomerization run. It is the overhead fluid fraction obtained when the total polymer oil is topped to meet a flash point of $\geq 400°$ F.

The weight ratio of short chain 1-olefin/long chain 1-olefin/recycle in the charge will be 0.9–1/1/0.1–0.2. The amount of boron trifluoride catalyst used will be between about 0.1% and about 5.0% by weight of the charge, preferably between about 1.5% and about 4%. The amount of water or alcohol promoter will be between about 0.01% and about 1.0% by weight of the charge. The oligomerization reaction is generally carried out at temperatures between about 0° C. (32° F.) and about 60° C. (140° F.), preferably between about 10° C. (50° F.) and about 50° C. (122° F.) for between one hour and about 4 hours.

EXAMPLE 1

This run was carried out to provide initial recycle stock and to illustrate the type of synthetic oil obtained when recycle is not used. The oligomerization was carried out using a mixture of propylene and mixed $C_{15-18}$ 1-olefins. After the run was completed and the catalyst was quenched, the total polymer oil, i.e., total reaction product, was topped using an 18" Vigruex column to 210° C., pot temperature, 125° C., head temperature at 1.0 mm Hg to produce finished oil having a flash point $\geq 400°$ F. Pertinent details and results are set forth in the Table.

The mixed $C_{15-18}$ olefins is a commercial mixture containing:

| C # | Wt. % |
|---|---|
| $C_{14}$ | 1 |
| $C_{15}$ | 29 |
| $C_{16}$ | 28 |
| $C_{17}$ | 27 |
| $C_{18}$ | 14 |
| $C_{19}$ | 1 |

EXAMPLE 1A

Total polymer oil, produced as described in Example 1, was distilled at 1 mm. mercury pressure until the residual (finished) oil had a flash point $\geq$ about 400° F. Seven fractions were collected over a boiling range of between about 50° C. and about 122° C. These 7 fractions were combined and represented the low-boiling recycle used in subsequent runs.

This recycle was subjected to Vapor Phase Chromatography. The results showed that there were no starting olefins present and that the recycle contained hydrocarbons ranging between about 18 and about 27 carbon atoms. The predominant portion contained between about 21 and about 24 carbon atoms. This is a typical recycle used in the improved process of this invention.

EXAMPLES 2 THROUGH 4

A series of runs was carried substantially as described in Example 1, except that recycle was added with the feed. In Example 2, the reycle came from Example 1, in Example 3 from Example 2 and in Example 4 from Example 3. Pertinent details and results are set forth in the Table.

Table

| Example | 1 | 2 | 3 | 4 |
|---|---|---|---|---|
| Total Feed, g. | 1237.8 | 1350.5 | 1350.5 | 1350.5 |
| Composition, % Wt. | | | | |
| Propylene | 49.1 | 44.9 | 44.9 | 44.9 |
| Chevron $C_{15-18}$ | 50.9 | 46.8 | 46.8 | 46.8 |
| Recycle | 0 | 8.3 | 8.3 | 8.3 |
| Reaction Conditions | | | | |
| Addition + Hold Time, hrs. | 1 + 1 | 1 + 1 | 1 + 1 | 1 + 1 |
| Reaction Temp, °C. | 48 | 48 | 46 | 43 |

Table-continued

| Example | 1 | 2 | 3 | 4 |
| --- | --- | --- | --- | --- |
| Catalyst BF$_3$, g. | 46.0 | 41.0 | 49.0 | 44.8 |
| Promoter n-BuOH, g. | 10.0 | 10.0 | 10.0 | 10.0 |
| Solvent n-Hexane, ml. | 500 | 358 | 500 | 500 |
| Quench NH$_4$OH, ml. | 45 | 45 | 45 | 45 |
| Conversion, % Olefin Feed | | | | |
| Total Polymer Oil | 87 | 100 | 100 | 100 |
| Finished Oil | 89 | 89 | 84 | 90 |
| Properties (Finished Oil) | | | | |
| Viscosity, cs. | | | | |
| 210° F. | 7.89 | 5.91 | 5.94 | 5.83 |
| 100° F. | 55.80 | 34.71 | 35.73 | 34.89 |
| Viscosity Index (VI) | 118 | 125 | 121 | 120 |
| Flash, °F. | 425 | 405 | 400 | 415 |
| Fire, °F. | 460 | 430 | 440 | 435 |
| Pour, °F. | 0 | +5 | +10 | +5 |

The data in the Table compare the results of the copolymerization of propylene and a mixed C$_{15-18}$-1-olefin via BF$_3$ catalysts with and without the benefit of recycle under comparable reaction conditions. Notably, at the same yield, the fluid viscosity was decreased about 25 percent over the control (from 8 cs. at 210° F. to about 6 cs.) whereas the viscosity index was improved when recycle was used. The slight pour point increase and the VI improvement give a strong indication that propylene-long chain olefin copoylmerization was favored over long chain olefin isomerization. The latter process produces internal olefins which, when incorporated into fluid polymers, cause undue molecular branching responsible for very poor VI properties.

The indications are that recycle seems to alter catalyst activity depending on choice of catalyst. This apparently has an effect not only on the amount of olefin double bond isomerization but also on the degree of polyimerization resulting in a lowering of average carbon number, in the case of BF$_3$.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. In a process for oligomerizing a short chain 1-olefin and a long chain 1-olefin having between 14 and 20 carbon atoms in the presence of boron trifluoride promoted by a minor amount of alcohol or water, at a temperature between about 0° C. and about 60° C.; the improvement in reducing viscosity and increasing the viscosity index of finished oil that results from the incorporation of a small amount of recycle using a weight ratio of short chain 1-olefin/long chain 1-olefin/recycle of 0.9–1/1/0.1–0.2; said recycle having a boiling range between about 50° C. and about 122° C. at 1.0 mm mercury pressure.

2. The process of claim 1, wherein said short chain 1-olefin is propylene and said long chain 1-olefin is a mixture of 1-olefins having 15 to 18 carbon atoms.

3. The process of claim 2, wherein the temperature is between about 10° C. and about 50° C.

4. The process of claim 2, wherein the amount of promoter is between about 0.1 percent and about 1.0 percent by weight of the charge.

* * * * *